US007858374B2

(12) United States Patent
Buchanan et al.

(10) Patent No.: US 7,858,374 B2
(45) Date of Patent: Dec. 28, 2010

(54) METHOD AND DEVICE FOR REDUCING POSITRON EMITTING ISOTOPE LABELED CARBON DIOXIDE TO POSITRON EMITTER ISOTOPE LABELED CARBON MONOXIDE VIA METAL OXIDE

(75) Inventors: Charles Russell Buchanan, Knoxville, TN (US); Andrew C. Williamson, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 747 days.

(21) Appl. No.: 11/803,388

(22) Filed: May 14, 2007

(65) Prior Publication Data

US 2008/0286873 A1 Nov. 20, 2008

(51) Int. Cl.
*G01N 23/00* (2006.01)
*C12M 1/00* (2006.01)

(52) U.S. Cl. ......................... 436/57; 436/165; 436/164; 422/129; 422/159

(58) Field of Classification Search ................ 436/165, 436/164, 57; 422/159, 129; 423/418.2, 415.1, 423/414; 376/199, 190, 156
See application file for complete search history.

(56) References Cited

U.S. PATENT DOCUMENTS 5,859,070 A * 1/1999 Jackson et al. .............. 518/713
2005/0142055 A1* 6/2005 Miyake et al. ........... 423/418.2

FOREIGN PATENT DOCUMENTS

EP 1 463 065 * 9/2004

OTHER PUBLICATIONS

Zeisler et al., Conversion of No-carrier-added [11C]carbon Dioxide to [11C]carbon Monoxide on Molybdenum for the synthesis of 11C-labelled Aromatic Ketones, 1997, Appl. Radit. Isot, vol. 48, No. 8, pp. 1091-1095.*

G Stocklin et al, Radiopharmaceuticals for Positron Emission Tomography; Methodical Aspects. Kluwer Academic Publishers. vol. 23, 1993, p. 123.*

* cited by examiner

*Primary Examiner*—Walter D Griffin
*Assistant Examiner*—Christine T Mui
(74) *Attorney, Agent, or Firm*—Peter L. Kendall

(57) ABSTRACT

A method and device for reducing positron emitter isotope labeled $CO_2$ to positron emitter isotope labeled CO generally includes introducing a volume of positron emitter isotope labeled $CO_2$ into a first heated reaction vessel comprising a metal oxide, such as Iron (II) Oxide such that the $CO_2$ is reduced to CO upon contact with the Iron (II) Oxide. The volume is then transferred to a second reaction vessel to remove any un-reacted $CO_2$, preferably, via a soda-lime trap. The volume is then transferred to a target, e.g., a storage vessel or subject. The $CO_2$ includes one of [$^{11}$C] or [$^{15}$O]. The first reaction vessel is, preferably, heated to a temperature of between 900 and 1000° C., and more preferably, to between 925 and 975° C., and even more preferably, to approximately 950° C. Preferably, the Iron (II) Oxide powdered and has a particle size of about −10 mesh.

25 Claims, 3 Drawing Sheets

METHOD AND DEVICE FOR REDUCING POSITRON EMITTING ISOTOPE LABELED CARBON DIOXIDE TO POSITRON EMITTER ISOTOPE LABELED CARBON MONOXIDE VIA METAL OXIDE

FIELD OF THE INVENTION

The instant invention relates generally to nuclear medicine and radio-labeled isotopes, and more specifically, to a method and device for reducing $CO_2$ to CO using metal oxide and synthesizing positron emitter radio-labeled molecular imaging probes comprising [$^{11}$C]CO or [$^{15}$O]CO as the positron emitter radio-label.

BACKGROUND OF THE INVENTION

Positron Emission Tomography (PET) is a powerful tool for diagnosing a number of health related conditions and detection of disease. Generally, PET imaging systems create images based on the distribution of positron-emitter isotopes in the tissue of a subject. The isotopes are typically administered to the subject by injection of probe molecules that comprise a positron-emitter isotope (radioisotopes, radionuclides), such as [$^{18}$F], [$^{11}$C], [$^{13}$N], or [$^{15}$O], which are attached to a molecule that is readily metabolized or localized in the subject, e.g., glucose, or that chemically binds to receptors within the subject. In some cases, the isotope can be administered to the subject as a solution or by inhalation.

Generally, radioisotopes are produced by bombarding a target material with a particle beam of a particle accelerator, e.g., a cyclotron. Thereafter, the radioisotopes are radiochemically processed into one or more radio-labeled molecular imaging probes for subsequent introduction into the subject. A number of devices for producing and automatically radiochemically synthesizing molecular imaging probes are known, for example, the Eclipse® line of cyclotrons and Explora® line of radiochemical-synthesizing devices and are known and are commercially available from Siemens Medical Solutions USA, Inc. of Malvern, Pa. Other examples of cyclotron, radiochemical synthesizing devices, e.g., gas processing units, and components therefor are described in U.S. Pat. Nos. 6,011,825 and 6,599,484 and U.S. Pat. Pub. Nos. 2002/0028177, 2005/0084055, 2006/0285623, and 2007/0043213, which disclosures are incorporated herein by reference.

An important factor in the production of radio-labeled molecular imaging probes is specific activity. Specific activity of a radioisotope or molecular imaging probe is the amount of radioactivity relative to the mass of the radioisotope or molecular imaging probe, and is often measured in Ci/μmol. The mass consists of all isotopic forms of the radioactive label. Accordingly, the specific activity can be affected by known synthesis processes, for example, the addition of stable isotopes during processing can result in dilution, or lowering of specific activity.

By way of example, in the case of $^{18}$F the maximum specific activity is 1,710 Ci/μmol. [$^{18}$F] fluoride ion produced by proton bombardment of a metal target filled with [$^{18}$O] water in a cyclotron typically has a specific activity of about 50-100 Ci/μmol, which represents up to a 40 to 1 dilution with stable [$^{19}$F] that is present in the [$^{18}$O] water and released from the metal target body and polymeric valves and tubing of the target delivery system. In general, [$^{18}$F] labeled molecular imaging probes prepared from [18F] fluoride ion have a specific activity of about 2-5 Ci/μmol after coupling of the [$^{18}$F] ion to a probe molecule, which illustrates that the radiochemical synthesis process results in another 25 to 1 dilution with stable [$^{19}$F]. Fluoride ion delivered from the cyclotron target will typically contain 0.2-0.4 μg (10-20 μmol) stable [$^{19}$F] fluoride ion along with the radioactive [$^{18}$F] fluoride ion. If the activity delivered is 1.0 Ci, the [$^{18}$F] fluoride ion mass will be about 9.0 ng or 0.5 nmol.

Similar issues arise when using [$^{11}$C] and other radioactive isotopes because known radiochemical synthesis processes are primary sources of unwanted [$^{12}$C] and other stable isotopes. For example, the maximum specific activity of [$^{11}$C] is 9,240 Ci/μmol. However, one current method of producing [$^{11}$C]CO is involves passing a volume of gas, e.g. [$^{11}$C]$CO_2$, over a packed bed of carbon and copper granules. As a result, the [$^{12}$C] carbon granules of the packed bed act as a source of contamination of the [$^{11}$C]CO and ultimately reduce the specific activity.

Accordingly, there is a need for a method and device for producing radio-labeled molecular imaging probes, and more specifically [$^{11}$C]CO and [$^{15}$O]CO, which exhibit higher specific activities while maintaining the simplicity and ease of current known devices and methods.

SUMMARY OF THE INVENTION

A method for reducing positron emitter isotope labeled $CO_2$ to positron emitter isotope labeled CO generally comprises contacting a volume of the positron emitter isotope labeled $CO_2$ with a metal oxide, such as Iron (II) oxide, to produce CO. In a preferred embodiment, the Iron (II) oxide is powdered and has a particle size of −10 mesh. In some embodiments, the $CO_2$ comprises [$^{11}$C] and a portion thereof is reduced to [$^{11}$C]CO. In other embodiments, the $CO_2$ comprises [$^{15}$O] and a portion thereof is reduced to [$^{15}$O]CO. In an embodiment, the $CO_2$ is introduced into the reaction vessel, which is heated to a temperature between 900 and 1000° C., and more preferably, to a temperature between 925 and 975° C., and even more preferably, to a temperature of about 950° C. In an embodiment, the method further comprises removing un-reacted $CO_2$ from the volume after the volume has contacted and substantially reacted with the Iron (II) oxide. In a preferred embodiment, removing of any un-reacted $CO_2$ is accomplished by introducing the volume into a soda-lime trap. In an embodiment, the CO that is produced is delivered to a target, such as a storage vessel or subject.

A device for reducing positron emitter isotope labeled $CO_2$ to positron emitter isotope labeled CO generally comprises a first heated reaction vessel comprising a metal oxide, such as Iron (II) oxide and a second reaction vessel comprising a $CO_2$ removing agent wherein a first continuous fluid comprising the positron emitter isotope labeled. $CO_2$ is introduced into the first heated reaction vessel to thereby reduce $CO_2$ to CO via the Iron (II) oxide. A second continuous fluid comprising $CO_2$ and CO is produced by the reaction is introduced into the second reaction vessel to remove any un-reacted $CO_2$ to form a third continuous fluid, which substantially comprises CO. The third continuous fluid is delivered to a target, such as a storage vessel or subject. In some embodiments of the device, the $CO_2$ comprises at least one of [$^{11}$C]$CO_2$ and [$^{15}$O]$CO_2$. In a preferred embodiment the first heated reaction vessel is heated to a temperature between 900 and 1000° C., and preferably, to a temperature between 925 and 975° C., and even more preferably, to a temperature of about 950° C. In a preferred embodiment, the Iron (II) oxide is in powder form and has a particle size of −10 mesh. In an embodiment, the $CO_2$ removing agent comprises a soda-lime trap.

BRIEF DESCRIPTION OF THE DRAWINGS

The invention will now be more fully described by way of example with reference to the accompanying drawings in which.

DETAILED DESCRIPTION OF THE INVENTION

The present invention will now be described and disclosed in greater detail. It is to be understood, however, that the disclosed embodiments are merely exemplary of the invention and that the invention may be embodied in various and alternative forms. Therefore, specific structural and/or functional details disclosed herein are not to be interpreted as limiting the scope of the claims, but are merely provided as an example to teach one having ordinary skill in the art to make and use the invention.

Figure 1:
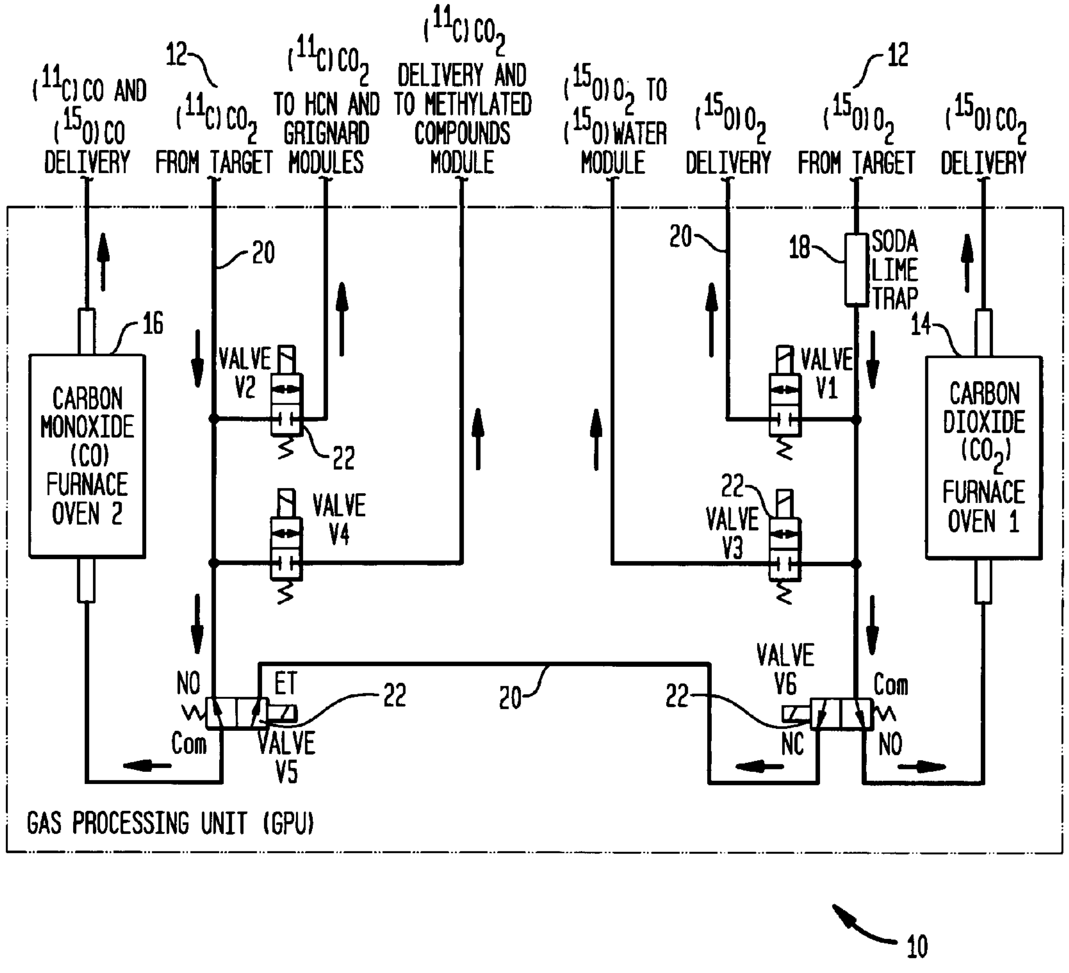
FIG. 1 (PRIOR ART)
FIG. 1 is a schematic illustration of a known radiochemical synthesizing device (gas processing unit) capable of automatically synthesizing [$^{11}$C]CO and [$^{15}$O]CO.

Referring now to the figures, FIG. 1 schematically illustrates a known gas processing unit (GPU) 10 capable of processing target gas 12. As previously indicated, an example of a known gas processing unit (GPU) includes the Explora® line of gas processing unit (GPU) commercially available from Siemens Medical Solutions USA, Inc. of Malvern, Pa. GPU 10 is capable of converting [$^{15}$O]$O_2$ target gases to [$^{15}$O]$CO_2$ and [$^{15}$O]CO and [$^{11}$C]$CO_2$ target gases to [$^{11}$C]CO. The GPU 10 also connects [$^{15}$O] and [$^{11}$C] target gases to other destinations. GPU 10 is typically mounted proximate a cyclotron (not shown) and within the shield thereof to allow easy transfer of the target gases. GPU 10 broadly comprises first furnace 14 and second furnace 16, each of which contain an amount of activated carbon. First furnace 14 contains a reaction vessel (not shown) having an amount of activated carbon and copper powder therein for producing $CO_2$ and second furnace 16 has a reaction vessel (not shown) containing activated carbon for producing CO. The copper powder contained in the first furnace is provided to remove any unreacted $O_2$. A soda lime trap 18 is illustrated as immediately following the source of the [$^{15}$O]$O_2$ target gas and serves to remove any carbon and/or vapor. It is also known to include a soda lime trap following the second furnace to remove any unreacted $CO_2$ from the [$^{11}$C]CO and [$^{15}$O]CO. Conduits 20, which can be made from stainless steel tubing, and computer controlled solenoid valves 22 are provided for routing the target gases throughout the various components of GPU 10. GPU 10 is typically controlled via a computer running a graphical user interface, such as Microsoft Windows®. First furnace 14 and Second furnace 16 each include a heating element (not shown) and contain reaction vessels (not shown), e.g., a quartz tube, which holds the activated carbon and/or activated carbon and copper. The reaction vessel connects to conduits 20 for passing a target gas through the furnaces. A temperature sensor and temperature controller (not shown) are typically provided for automatically controlling the temperature of the furnaces and other operations. Typically, the first furnace operates at a temperature of 500° C. to convert [$^{15}$O]$O_2$ to [$^{15}$O]$CO_2$ and the second furnace operates at a temperature of 950° C. to convert either [$^{11}$C]$CO_2$ to [$^{11}$C]CO or [$^{15}$O]$CO_2$ to [$^{15}$O]CO. Accordingly, radiochemical synthesis of [$^{11}$C]CO using GPU 10, which involves passing a volume of [$^{11}$C]$CO_2$ over the carbon and copper granules, results in contamination of the final product by the [$^{12}$C]C of the carbon and copper granules, which reduces specific activity. Similar reductions in specific activity occur in the preparation of [$^{15}$O]CO from a [15O]$O_2$ target gas.

Figure 3:
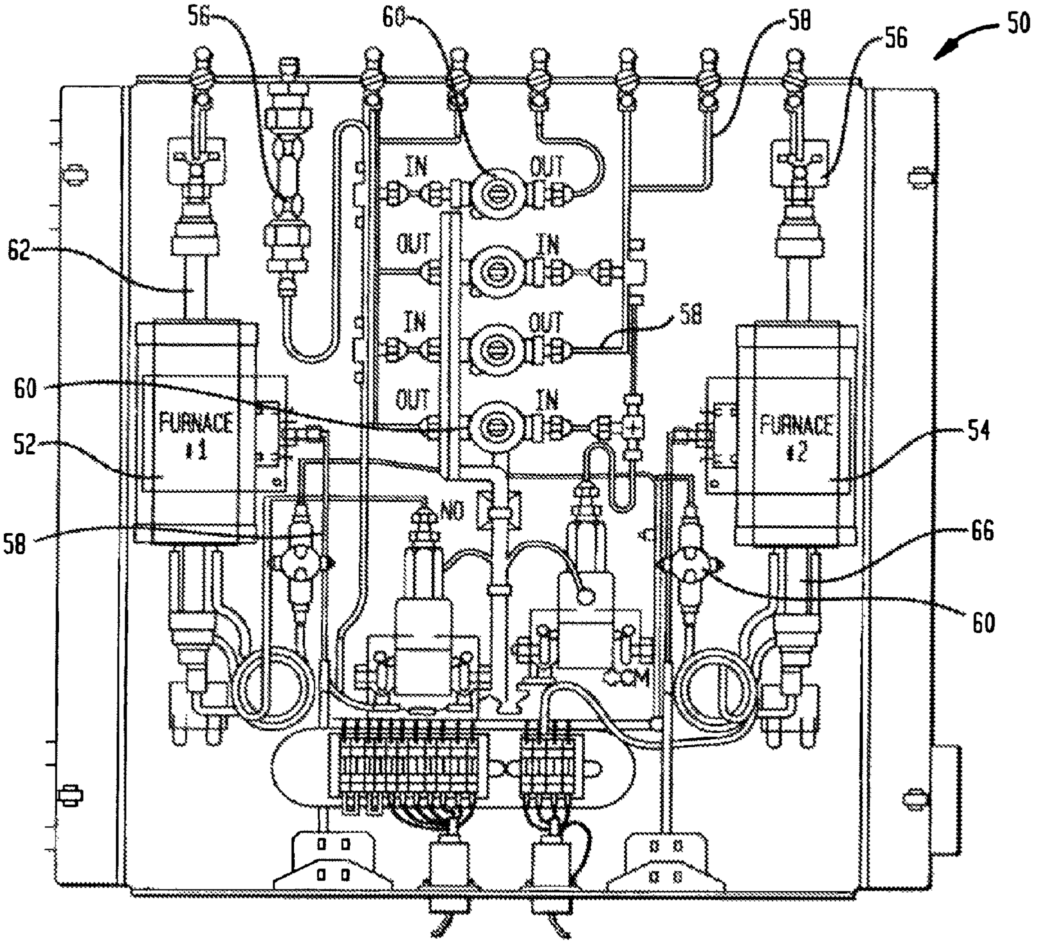

Referring now to FIG. 3, the instant invention broadly relates to an apparatus and method for forming CO using Iron (II) Oxide. In this regard, GPU 50, according to the instant invention, includes a first furnace 52, a second furnace 54 and one or more soda lime traps 56 for removing carbon and/or vapor from a gas stream. Similar to GPU 10, GPU 50 according to the invention includes a plurality of conduits 58, which can be made from stainless steel tubing, and computer controlled solenoid valves 60. Solenoid valves 60 are provided for automatically routing the various targets gases and product gases throughout the various components of GPU 50. GPU 50 can be controlled via a computer running a graphical user interface, such as Microsoft Windows®. First furnace 52 is similar to that described above with regard to GPU 10 in that it includes a heating element (not shown) and a reaction vessel 62, which contains an amount of activated charcoal. Reaction vessel 62 can be formed from quartz tubing. As described above, first furnace 52 is typically heated to a temperature of approximately 500° C. and is configured for converting [$^{15}$O]$O_2$ to [$^{15}$O]$CO_2$, which can be used for the production of [$^{15}$O]CO.

Figure 2:
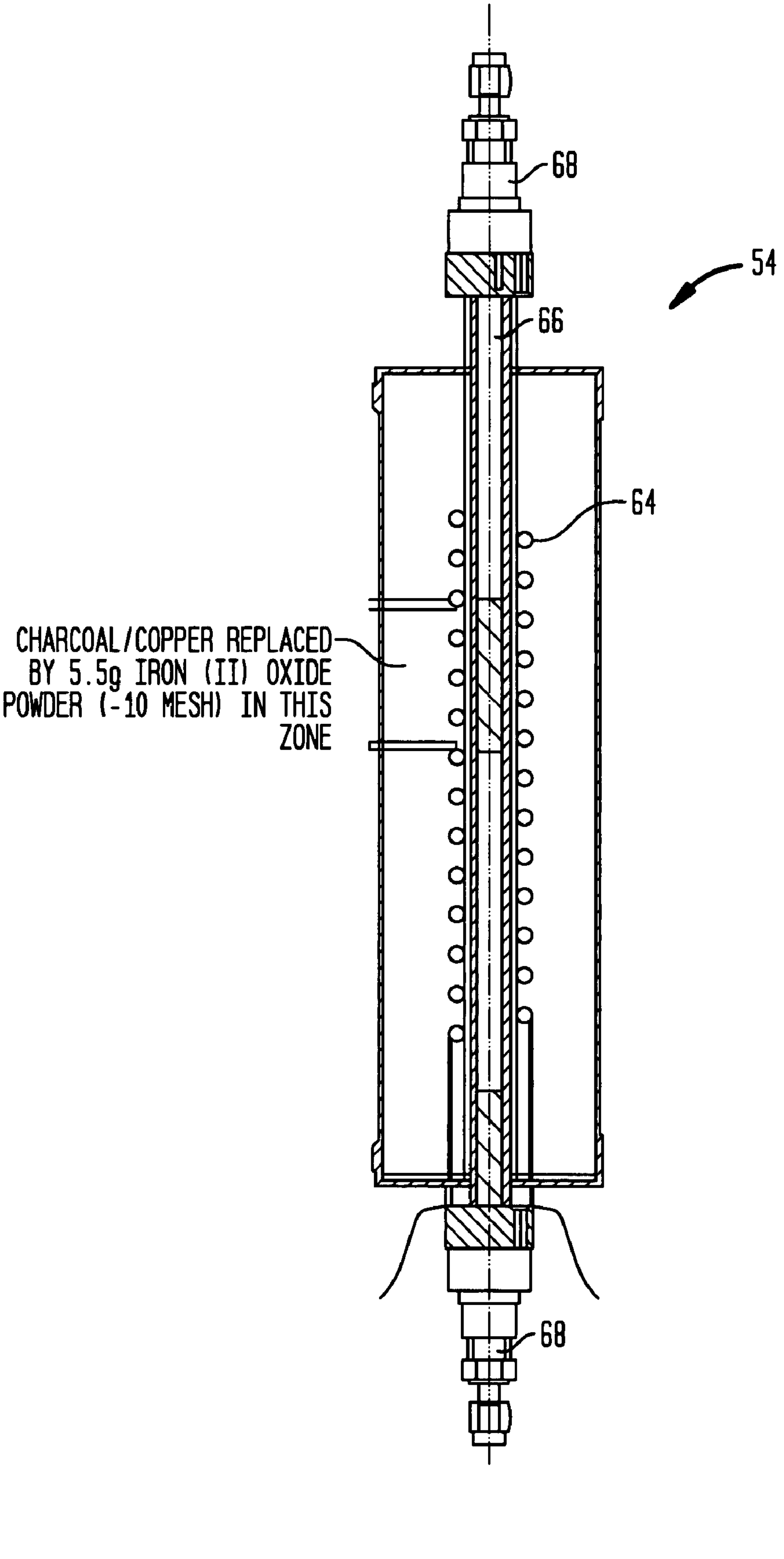
FIG. 2 is a schematic illustration of a reaction vessel according to the invention; and, FIG. 3 is a schematic illustration of a radiochemical synthesis device according to the invention.

By contrast, as shown in FIGS. 2 and 3, second furnace 54 comprises heating element 64 and includes reaction vessel 66. Reaction vessel 66 can be formed from quartz tubing and is configured to contain an amount of Iron (II) Oxide and/or quartz wool. In the embodiment shown in FIG. 2 the iron (II) oxide packing is illustrated as being substantially centrally disposed along the length of reaction vessel 66 and heating element 64 is disposed thereabout. Reaction vessel 66 and reaction vessel 62 each include couplers 68 at each of the ends thereof for coupling the reaction vessels to the conduits 58 of the GPU 50. Couplers 68 can comprise quick release type coupling devices and include O-rings for sealing the interface between the reaction vessel and the conduit. In a preferred embodiment, the Iron (II) Oxide is powdered and has a particle size of −10 mesh. The furnace and reaction vessel 66 are preferably heated to between 900-1000° C., and more preferably, to between 925 and 975° C., and even more preferably, to approximately 950° C.±5° C., prior to the introduction of a target gas into the furnace/reaction vessel, e.g., $CO_2$. Accordingly, when an amount of $CO_2$ gas, e.g., [$^{11}$C]$CO_2$ or [$^{15}$O]$CO_2$, is introduced into reaction vessel 66 that has been heated to between 900 and 1000° C., the $CO_2$ gas is reduced to CO by reaction with the Iron (II) Oxide. Such reaction occurs without the contamination of added [$^{12}$C]C as with reduction using activated charcoal and copper. Thereafter, the converted CO gas can be passed though soda lime trap 56 to remove any unreacted $CO_2$ from the stream and can then be delivered to a storage container and/or a subject.

As shown in the following tables, experiments comparing yield and saturation percentages of a target gas using the inventive Iron (II) Oxide packing, carbon and copper packing, molybdenum wire packing and molybdenum powder packings show that the Iron (II) Oxide packing, surprisingly and unexpectedly, exhibits substantially equivalent conversion and saturation yields as carbon/copper packings, which packings serve as the benchmark of commercially viable products. When compared with molybdenum wire and molybdenum powder packings, which are not deemed to be commercially viable, the Iron (II) Oxide packings show much greater conversion and saturation yields. The experiments were conducted using cyclotron DV-91 and a production Siemens GPU assembly (Model No: 3601001-00). $CO_2$ gas was introduced into a heated furnace/reaction vessel containing the specifically identified packing configuration. The % conversions and saturation yields of CO were then determined from the reaction products.

Experimental Results:

CARBON & COPPER

| Packing Configuration | Time (Min.) | Current (μA) | Temp (C.) | # of Runs | % Conversion | Sat. Yield |
|---|---|---|---|---|---|---|
| Carbon & | 5 | 60 | 950 | 2 | 66 | 61.5 |
| Copper | 5 | 60 | 975 | 2 | 74 | 57 |
| | 5 | 60 | 1000 | 1 | 74 | 32 |

MOLYBDENUM

| Packing Configuration | Time (Min.) | Current (μA) | Temp (C.) | # of Runs | % Conversion | Sat. Yield |
|---|---|---|---|---|---|---|
| 2.1 g | 5 | 60 | 750 | 1 | ~2 | 59.7 |
| Molybdenum | 5 | 60 | 800 | 2 | ~2 | 58.7 |
| Wire | 5 | 60 | 850 | 1 | ~2 | 57 |
| | 5 | 60 | 900 | 1 | ~2 | 59.4 |
| | 5 | 60 | 950 | 1 | ~2 | 57.5 |
| 3.8 g | 5 | 60 | 700 | 1 | ~5-6 | 58.6 |
| Molybdenum | 5 | 60 | 725 | 1 | ~5-6 | 57.6 |
| Wire | 5 | 60 | 750 | 1 | ~5-6 | 58.4 |
| | 5 | 60 | 775 | 1 | ~5-6 | 60 |
| | 5 | 60 | 800 | 1 | ~5-6 | 63.4 |
| | 5 | 60 | 825 | 1 | ~5-6 | 58 |
| | 5 | 60 | 840 | 1 | ~5-6 | 61.5 |
| | 5 | 60 | 850 | 3 | ~5-6 | 60.1 |
| | 5 | 60 | 875 | 1 | ~5-6 | 68 |
| 7 g Molybdenum | 5 | 60 | 875 | 2 | 50 | 58 |
| Powder | 5 | 60 | 850 | 2 | 40 | 62 |
| | 5 | 60 | 875 | 3 | 43 | 63 |

Iron (II) Oxide

| Packing Configuration | Time (Min.) | Current (μA) | Temp (C.) | # of Runs | % Conversion | Sat. Yield |
|---|---|---|---|---|---|---|
| 5.5 g FeO | 5 | 60 | 950 | 4 | 68 | 62.2 |
| Powder | 5 | 60 | 975 | 1 | 68 | 68 |
| | 5 | 60 | 1000 | 1 | 67.1 | 58 |
| | 40 | 60 | 975 | 1 | 63.2 | 52 |

It is thus seen that the use of an Iron (II) Oxide packing according to the invention to reduce $[^{11}C]CO_2$ or $[^{15}O]CO_2$ to CO results in the formation of a CO gas having an equivalent conversion and saturation yield when compared with CO produced using carbon and copper packings, but which inherently has a greater specific activity as the result of the removal of carbon in the reduction of $CO_2$ to CO— all while maintaining the simplicity and ease of current known devices and methods. It will be recognized that although the invention has been described using Iron (II) oxide as a reactant, other metal oxides may be used as appropriate.

It should be appreciated by those having ordinary skill in the art that while the present invention has been illustrated and described in what is deemed to be the preferred embodiments, various changes and modifications may be made to the invention without departing from the spirit and scope of the invention. Therefore, it should be understood that the present invention is not limited to the particular embodiments disclosed herein.

What is claimed is:

1. A method for reducing positron emitter isotope-labeled $CO_2$ to positron emitter isotope-labeled CO, said method comprising:

contacting a volume of said positron emitter isotope labeled $CO_2$ with Iron (II) oxide to produce CO.

2. The method of claim 1 wherein said Iron (II) oxide is powdered.

3. The method of claim 1 wherein said $CO_2$ comprises $[^{11}C]$ and a portion thereof is reduced to $[^{11}C]CO$.

4. The method of claim 1 wherein said $CO_2$ comprises $[^{15}O]$ and a portion thereof is reduced to $[^{15}O]CO$.

5. The method of claim 3 wherein said $CO_2$ is introduced into a reaction vessel and said reaction vessel is heated to between 900 and 1000° C.

6. The method of claim 5 wherein said reaction vessel is heated to between 925 and 975° C.

7. The method of claim 6 wherein said reaction vessel is substantially heated to 950° C.

8. The method of claim 1 further comprising removing un-reacted $CO_2$ from said volume after said contacting.

9. The method of claim 8 wherein said removing is accomplished by introducing said volume into a soda-lime trap.

10. A method for reducing positron emitter isotope-labeled $CO_2$ to positron emitter isotope-labeled CO, said method comprising:

introducing a continuous fluid stream comprising positron emitter isotope labeled $CO_2$ into a first heated reaction vessel containing Iron (II) oxide, said Iron (II) oxide producing CO by the reduction of said $CO_2$;

introducing a continuous fluid stream comprising any un-reacted $CO_2$ and said CO into a second reaction vessel, said second reaction vessel comprising an agent for removing said un-reacted $CO_2$; and delivering said positron emitter isotope labeled CO to a target.

11. The method of claim 10 wherein said reaction vessel is heated to a temperature between 900 and 1000° C.

12. The method of claim 11 wherein said reaction vessel is heated to a temperature between 925 and 975° C.

13. The method of claim 12 wherein said reaction vessel is heated to a temperature of about 950° C.

14. The method of claim 10 wherein said second reaction vessel comprises a soda-lime trap.

15. The method of claim 10 wherein said $CO_2$ comprises at least one of $[^{11}C]CO_2$ and $[^{15}O]CO_2$.

16. The method of claim 15 wherein said target is a test subject.

17. The method of claim 10, wherein said Iron (II) oxide is powdered.

18. A device for reducing positron emitter isotope labeled $CO_2$ to positron emitter isotope labeled CO, said device comprising:

a first heated reaction vessel comprising Iron (II) oxide; and a second reaction vessel comprising a $CO_2$ removing agent;

wherein a first continuous fluid comprising said positron emitter isotope labeled $CO_2$ is introduced into said first heated reaction vessel to thereby reduce $CO_2$ to CO via said Iron (II) oxide to produce a second continuous fluid comprising $CO_2$ and CO, and wherein said second continuous fluid is introduced into said second reaction vessel to remove any un-reacted $CO_2$ from said second continuous fluid thereby forming a third continuous fluid substantially comprising CO, and wherein said third continuous fluid is delivered to a target.

19. The device of claim 18 wherein said $CO_2$ comprises at least one of $[^{11}C]CO_2$ and $[^{15}O]CO_2$.

20. The device of claim 18 wherein said first heated reaction vessel is heated to between 900 and 1000° C.

21. The device of claim 18 wherein said first heated reaction vessel is heated to between 925 and 975° C.

22. The device of claim 18 wherein said first heated reaction vessel is heated to about 950° C.

23. The device of claim 18 wherein said Iron (II) oxide is in powder form.

24. The device of claim 23 wherein particle size of said Iron (II) oxide is −10 mesh.

25. The device of claim 18 wherein said $CO_2$ removing agent comprises a soda-lime trap.

* * * * *